United States Patent [19]

Fell

[11] Patent Number: 5,073,172
[45] Date of Patent: Dec. 17, 1991

[54] DEVICE FOR ASPIRATING WOUND FLUIDS

[75] Inventor: Helmut Fell, St. Ingbert, Fed. Rep. of Germany

[73] Assignee: Medinorm Aktiengesellschaft medizintechnische Produkte, Quierschied, Fed. Rep. of Germany

[21] Appl. No.: 415,269

[22] PCT Filed: Jan. 19, 1988

[86] PCT No.: PCT/DE88/00022
§ 371 Date: Sep. 25, 1989
§ 102(e) Date: Sep. 25, 1989

[87] PCT Pub. No.: WO88/05319
PCT Pub. Date: Jul. 28, 1988

[30] Foreign Application Priority Data

Jan. 20, 1987 [DE] Fed. Rep. of Germany ....... 3701386
Apr. 2, 1987 [DE] Fed. Rep. of Germany ....... 3711093
Jul. 24, 1987 [DE] Fed. Rep. of Germany ....... 3724483
Oct. 30, 1987 [DE] Fed. Rep. of Germany ... 8714456[U]

[51] Int. Cl.$^5$ .................................................. A61M 1/00
[52] U.S. Cl. ...................................... 604/119; 604/119
[58] Field of Search ............... 604/319, 326, 335, 331, 604/119

[56] References Cited

U.S. PATENT DOCUMENTS

3,624,821 11/1971 Henderson ........................... 604/119
3,946,770 3/1976 Trinne et al. ............................ 141/5
4,112,949 9/1978 Rosenthal et al. ................... 604/319
4,372,336 2/1983 Cornell et al. ....................... 604/319

Primary Examiner—Randy C. Shay
Assistant Examiner—G. Gualtieri
Attorney, Agent, or Firm—Collard, Roe & Galgano

[57] ABSTRACT

A suction bottle for aspirating would secretions containing a small quantity of a pressure-adjusting liquid selected so that its vapor pressure conforms to a desired vacuum level. The vacuum level is maintained until the suction bottle is almost completely filled. If the liquid dissolves in the aspirated secretions, the vacuum level will decrease. The vacuum level can be varied by changing the temperature. The bottled can be made with thinner walls than bottles used heretofore because the risk of deformation during sterilizing is reduced as the inside pressure rises with the increase in temperature. For the purpose of connecting a suction bottle with a connecting tube joined with a wound draining system, provision is made for a connection system embodied as a suction controlling device.

14 Claims, 5 Drawing Sheets

DEVICE FOR ASPIRATING WOUND FLUIDS

BACKGROUND OF THE INVENTION

The invention relates to a device for aspirating fluids from wounds, in particular to parts on and for such devices. Such devices and parts thereof are used in the drainage of wounds. For this purpose, a pre-evacuated suction bottle preferably equipped with a vacuum indicator is connected via a connecting tube with a perforated drainage tube which is inserted in the cavity of the wound, the latter being sealed airtight.

PRIOR ART

Suction bottles, as a rule, are adjusted by the manufacturer to about five to ten percent of the normal air pressure, and typically have a holding capacity of 150 to 1000 ml. The internal pressure is indicated via a vacuum indicator. If the suction force is to be low, the bottle, which has been evacuated to a relatively high degree by the manufacturer, is partly aerated before it is connected to the connecting hose.

If the bottle, when in use, fills with secretion, the pressure of the air in the residual volume rises gradually according to Boyle-Mariotte's rule. At a starting pressure in the empty bottle of five percent of the atmospheric pressure, the pressure difference between the inside and outside comes to 95 percent of the atmospheric pressure. If the bottle fills halfway, its inside pressure doubles, so that the pressure difference comes to 90 percent of the atmospheric pressure. With a bottle filled to 75 percent of its capacity, the pressure difference between the inside and outside still comes to 80 percent of the atmospheric pressure. This calculation is an approximation that does not take into account the vapor pressure of the secretion, which, however, is low as compared to the air pressure. From the empty bottle to the bottle three-quarters full of secretion, the suction of the system is thus quite even, which is important for the efficiency. However, the range of a uniform suction effect becomes considerably poorer if the bottle, which is empty with respect to secretion, has been partly aerated in order to obtain a low suction effect. In addition to this shortcoming, the bottle partly aerated by the user has the drawback that there is the risk of contamination. Therefore, manufacturers also supply suction bottles with an inside pressure corresponding to about 50 percent of the atmospheric pressure.

It is deemed desirable not only that the inside pressure can be adjusted and maintained as constant as possible, but also that the pressure can be read as accurately as possible. Various solutions have become known for these purposes. Most frequently used is a plastic bellows, which is mounted on the suction bottle and operates in a transparent hollow cylinder with a scale. It has been found, however, that the reading accuracy of the bellows is insufficient. Hence indicators with mechanical springs have been proposed as well. Such an indicator is known from DE-C2-30 11 163.

As stated above, the device according to the invention is used in association with a pre-evacuated suction bottle, which is connected with a perforated wound draining tube via a connecting tube.

The connecting device normally used is a simple tube, of which the one end is connected to a connection fitting on the suction bottle, and the other end is connected to a connection fitting on the wound draining tube. A clamping device is used for interrupting this system, i.e., for closing off the tube.

When a perforated wound draining tube is connected with a suction bottle by way of a connecting tube and the passage through the latter is opened by releasing the mentioned clamping device, the full vacuum of the preevacuated suction bottle is applied to the cavity of the wound. So that the suction is not too strong especially with fresh wounds, the manufacturers of suction bottles supply bottles which are already partly aerated. Their suction effect, however, falls off quickly once they fill with secretion.

Therefore, it is deemed desirable within the framework of the invention to propose a connection system that permits superior handling than the familiar connecting tube.

SUMMARY OF THE INVENTION

Devices according to the invention have a system for keeping the vacuum in a bottle constant substantially throughout the entire filling process.

A first possibility for concretizing such a system is to use a bottle with a small quantity of a liquid of which the vapor pressure conforms to the desired vacuum. If a liquid is used that dissolves in the aspirated secretion, the result is that the vapor pressure decreases based on the law of vapor pressure reduction, particularly because the vapor pressure of the secretion is very low, to begin with. This means that the suction effect becomes stronger as the bottle fills and the wound heals, which is desirable. With the suction bottles known heretofore, it was not possible to achieve such increase in the suction power.

A second possibility for realizing such a system is to fill the bottle up to the desired vacuum with a gas that dissolves in the aspirated secretion and/or enters into a chemical bond with the latter. It is especially beneficial if a gas is used of which, in a certain secretion volume, the same volume of gas dissolves, or a volume of gas greater than the volume corresponding with the volume of the secretion. Again, the result is that the vacuum remains constant or becomes higher instead of falling off as the bottle fills, as was the case heretofore.

With the embodiments according to the first and second possibilities, the suction vacuum can be adjusted by changing the temperature. With conventional suction bottles, it was not possible to adjust the vacuum while a suction bottle was in operation. Such models offer the further advantage that the bottles have greater stability against deformation at elevated temperatures, for example when they are sterilized.

A third possibility for realizing such a system is to use a vacuum reducer, that is, a mechanical component which, on the suction side, reduces the vacuum in the interior of the bottle to such an extent that only the desired suction vacuum is maintained. A vacuum reducer must not necessarily be rigidly mounted on a suction bottle. It can be arranged at any desired point between a suction bottle and a wound draining tube. In the present case, not the suction bottle but the total system is characterized in that it provides for a constant suction vacuum on the wound.

Particularly advantageous embodiments of vacuum reducers are described hereinafter. Such vacuum reducers reflect the entire inventive idea of constructing a wound drainage system in a way such that a desired suction vacuum can be maintained at a constant level.

A preferred design of a vacuum reducer has, as the valve part in the reducer, a piston running in a hollow cylinder. Such a piston can be used at the same time for indicating the rising pressure, as it occurs when a suction bottle is almost filled up. If such pressure indication is desired in a wound drainage system in which keeping the pressure constant is not what matters, the vacuum reduction function of such component can be dispensed with and only the piston in the hollow cylinder is used for indicating the pressure.

Instead of using a piston as the valve in the vacuum reducer, it is possible to make use of a finger-shaped, flexible diaphragm. Like the afore-mentioned piston, this diaphragm, too, may function as the pressure indicator, whereby it is possible to realize a particularly conspicuous color indication of the pressure. Hence such a component offers a special advantage even if used only as a vacuum indicator without the pressure reduction function.

The connection system according to the invention is characterized in that it is designed as a suction controller, for which purpose it has a diaphragm that opens or closes a center opening in a diaphragm holder depending on the pressures acting on its inside and outside surfaces. The pressure on the outer side can be adjusted by guiding the diaphragm holder with the diaphragm sealed in a hollow cylinder, the latter being closed at the end on the side where the diaphragm is disclosed. Preferably, the diaphragm is shifted back and forth via a rotary motion guided by a screw thread between the diaphragm holder and the hollow cylinder.

According to another advantageous design, the end wall of the hollow cylinder has, in the center on the inside, an elastic sealing part, which presses against the diaphragm when the diaphragm holder is completely shifted against the sealed end of the hollow cylinder, which causes the diaphragm to be forced against the center opening in the diaphragm holder, sealing the opening. In this way, it is possible to break the connection between a suction bottle, which is connected to the center opening, and the wound draining tube.

In addition to the connection with the center opening for the suction bottle and the connection for the wound draining tube, the diaphragm holder preferably has additional connection fittings for a vacuum indicator device and/or for an overflow receptacle, into which the secretion of the wound drains as long as the center opening is closed. Such a plurality of openings may be present also in a connection device in which the diaphragm is not displaceable in the hollow cylinder, as described, for example, in German Patent Application 37 24 483.

DETAILED DESCRIPTION OF THE PREFERRED EMBODIMENTS

Figures 1, 2:
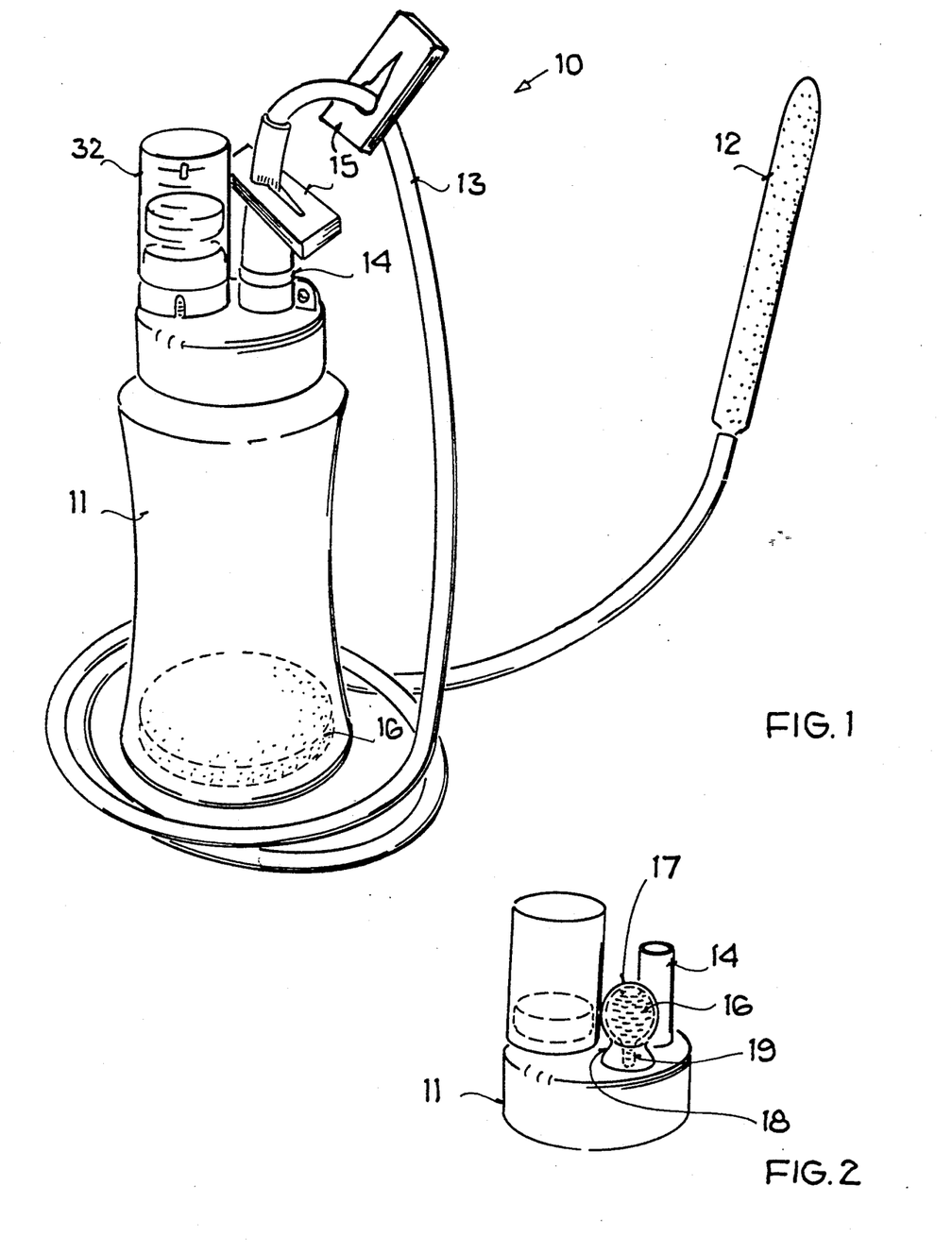
FIG. 1: is a perspective view of a wound drainage system with a suction bottle containing a small quantity of liquid with a predetermined low vapor pressure.
FIG. 2: is a perspective view of the top part of a suction bottle according to FIG. 1, but comprising an additional space for receiving an ampule with a liquid with low vapor pressure.

The suction system 10 shown in FIG. 1 has a suction bottle 11 and a wound draining tube 12, which is connected with the suction bottle 11 by pushing a connecting tube 13 over a suction fitting 14 on the suction bottle 11, and connecting the wound draining tube 12 to the other end of the connecting tube. The end of the connecting tube 13 on the bottle side and the rubber connection piece for connecting such tube to the bottle can be squeezed off via the hose clamps 15, which is done for changing the bottle.

As opposed to conventional systems, the interior space of the suction bottle 11 does not contain air under low pressure, but a lowest possible volume of a liquid 16, which is in equilibrium with its gas phase, hence with its saturated vapor. The vapor fills the remaining volume of the suction bottle 11.

The vapor pressure of a liquid is known not to be dependent upon the volume of the vapor if the liquid phase is present. The liquid 16 to be put in the suction bottle 11 is selected according to the desired degree of vacuum. If the inner suction pressure at room temperature is to amount to, for example 50 percent of the normal atmospheric pressure, a mixture of 50 percent pentane and 50 percent hexane can be used advantageously. If the share of pentane is increased, a weaker suction effect is obtained. If the share of hexane is increased, the suction effect increases and the inner suction pressure hence decreases. A volume of about 1 ml in a 600 ml bottle suffices to fill the entire bottle with vapor. Preferred is an amount of about 5 ml.

The course of the pressure development during the filling of the suction bottle 11 with wound secretion depends on whether the liquid 16 loaded in the bottle is soluble in the secretion of the wound or not, and, if it is soluble therein, on the ratio of the volumes of the liquid 16 and the secretion of the wound. If the liquid 16 is only slightly or not at all soluble in the secretion of the wound, the inner suction force remains constant for the most part as the suction bottle 11 fills with secretion, i.e., it is independent of the filling volume. This means that the volume of the bottle can be completely utilized in spite of a higher starting pressure, as opposed to the conditions found with air-filled bottles with increased starting pressure. If the liquid 16 loaded in the bottle is soluble in the secretion of the wound, the vapor pressure in the suction bottle 11 decreases as the filling degree increases, which is to say, such vapor pressure follows Raoult's law of vapor pressure reduction, which states that the relative vapor pressure reduction at constant temperature is equal to the ratio of the number of dissolved molecules to the total number of molecules. Hence, in the case of solubility, the inner suction pressure of the bottle 11 decreases as the bottle increasingly fills with secretion, i.e., the suction effect of the bottle is stronger. Such increase of the suction effect with the increasing filling conforms to the desired ideal course, that is, the suction effect is low while the wound is fresh, and grows when the wound gets older. In this case, too, the volume of the suction bottle 11 is well utilized.

Another advantage of a suction bottle 11 with the liquid 16 is that the inner suction pressure can be controlled by changing the temperature. If the temperature of the suction bottle 11 is raised, in the simplest case by mounting it close to the body of the patient, the suction effect becomes lower because the inside pressure rises. If the bottle is cooled, its suction effect is greater.

A suction bottle with pressure-adjusting liquid offers advantages in connection with sterilization processes as well. Conventional suction bottles have to be manufactured with relatively thick walls, so that the plastic material, which becomes softer at elevated temperatures, is capable of withstanding the pressure difference between the inside and outside also during the sterilization. In gas sterilization, which is applied in most cases, a temperature of about 35 degrees Celsius is used with the known bottles in most instances. A higher temperature, though, would be more favorable, but the thermoplastics used for making the bottles could not survive higher temperatures without deformation. With suction bottles with liquid, the bottle 11 has a higher inside pressure than the highly evacuated bottles used heretofore even at room temperature. This pressure rises further as the bottle heats up during the gas sterilization, and, at the boiling point of the liquid 16, is becomes equal the atmospheric pressure, so that the bottle 11 is not loaded in any way with pressure. Hence the bottle 11 can have thinner walls than conventional bottles and yet be heated to higher temperatures during sterilizing. With the afore-mentioned mixture of 50 percent pentane and 50 percent hexane, the boiling point at atmospheric pressure is at about 50 degrees Celsius, so that it is possible without any problems to apply sterilizing temperatures significantly above the temperatures of around 35 degrees Celsius used heretofore.

Organic liquids can be considered almost exclusively as the pressure-adjusting liquids 1. Such liquids quite generally raise the problem of compatibility with the thermoplastic material of the suction bottle 11. Most organic liquids attack such plastics, though only at a very low rate. Adhesives of the type used for joining various parts of a suction bottle are gradually attacked as well. Drawbacks resulting from such corrosion are avoided by a model according to FIG. 2, in which an elastic cap 17 is present on the top of the suction bottle 11, which cap is communicatively connected with the interior space of the suction bottle 11 by way of a connection fitting 18. The elastic cap 17 contains a glass ampule 19 containing a vapor pressure-adjusting liquid 16, of which a predetermined quantity is melted into such ampule. With the undamaged ampule 19, the system operates like a conventional suction bottle. If the suction force has to be reduced without partly aerating the system and thus without reducing the volume of secretion that can be aspirated, the ampule 19 is crushed, which releases the liquid 16, which fills the suction bottle 11 with its vapor until the equilibrium is established between the vapor pressure of the liquid and the inside pressure in the suction bottle 11. In this way, the situation shown in and described for FIG. 1 is obtained.

Instead of filling the suction bottle 11 according to FIG. 1 with the vapor of a small amount of a liquid 16, it is possible also to fill the suction bottle 11 with a gas up to the desired inner suction pressure, e.g. 50 percent atmospheric pressure, which gas dissolves in the secretion of the wound and/or enters into a chemical bond with the latter. Primarily $CO_2$ is considered in this case, which is very well soluble in water and hence in wound secretion as well. Depending on the temperature and the predetermined $CO_2$-pressure, the amount of $CO_2$ absorbable by a certain volume of secretion is greater than or approximately equal the amount of such secretion volume. In the present case, the inside pressure drops as the secretion filling increases, or it remains constant In practical applications it is important to be aware of the fact that the equilibrium between the dissolution pressure of the filled gas and the vapor pressure of the gas is reached only gradually. This, however, is frequently unimportant because wound secretion is, as a rule, drained only very slowly. In exceptional cases, in which a relatively large quantity of wound secretion is collected at a relatively high rate, the suction bottle 11 has to be moved, so that the gas can be absorbed by the secretion of the wound as quickly as possible.

The suction bottles 11 filled with a gas of the described type at the predetermined pressure, too, offer the advantage that the vacuum suction is adjustable by changing the temperature, and that the risk of changing the shape of the bottle during sterilizing is reduced.

The Applicant has invented suction bottles in connection with which the afore-described addition of liquid or gas is especially advantageous when the bottle is sterilized. Such bottles, too, are the object of the present application as well. Such suction bottles are bottles with a bottom which can be pierced through by a cannula. As materials for the bottom, all materials of the type used in medical technology as diaphragms for piercing with cannulas can be considered. According to a preferred design, the bottom of a bottle according to the invention consists of latex. Such bottle is joined with the thermoplastic body of the bottle by glueing. The latex bottom can be pierced by the cannula of a transfusion apparatus. It is possible in this simple way to recycle aspirated wound secretion into the circulation of the patient.

When such a suction bottle is used together with a liquid of the type described above, or with a gas filling of the type described above, the advantage is that there is no risk that the bottom tears off or tears during sterilizing under the effects of the vacuum and elevated temperature. However, it has to be pointed out, furthermore, that such a bottle with a bottom capable of being pierced by a cannula is also highly advantageous if it is used like a conventional suction bottle as an evacuated bottle without any measures for maintaining the inside pressure constant.

Figure 3:
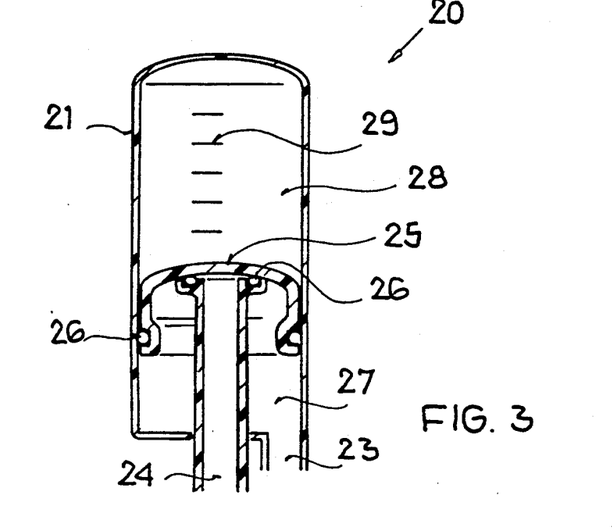
FIG. 3: is a longitudinal section through a vacuum reducer in a position in which it functions as the pressure reducer.
Figure 4:
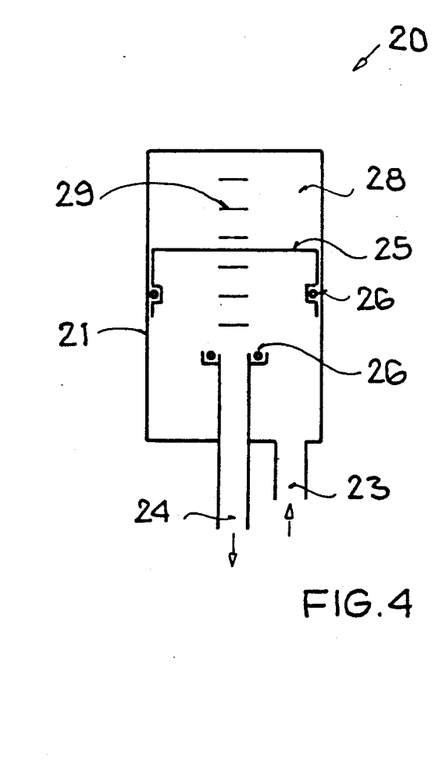
FIG. 4: is a schematic longitudinal section through the vacuum reducer according to FIG. 3, but shown in a position in which it functions as the pressure indicator.

The vacuum prevailing on a wound draining tube 12 can be kept constant also by a vacuum reducer 20 according to the embodiment shown in FIGS. 3 and 4. Such vacuum reducer 20 can be mounted either rigidly on a suction bottle 11, or interconnected at any desired point between the suction fitting 14 and the wound draining tube 12, as a separate component in the connection between the wound draining tube 12 and the suction bottle 11. This applies to all vacuum reducers.

The vacuum reducer 20 according to FIGS. 3 and 4 has a hollow cylinder 21, which is closed at the top. At the bottom, the hollow cylinder 21 is closed by a bottom 22, the latter being penetrated by an outward leading inlet fitting 23, which does not project inward, and a shutoff fitting 24 protruding into the interior of the cylinder, such fittings being sealed tight. A piston 25, which is sealed against the inside wall of the hollow cylinder 21 by an O-ring 26, runs in the interior of the cylinder. Instead of an O-ring 26 it is advantageously possible also to use a gasket directly molded on the wall guiding the piston.

In the starting condition of the vacuum reducer 20, the piston 25 is disposed closely below the upper end of the hollow cylinder 21. The above-mentioned components enclose a small volume of gas. Now, when the shutoff fitting 24 is first placed on the suction fitting that is clamped by a tube clamp 15 (FIG. 1) and the connecting tube 13 is subsequently pushed over the inlet fitting 23 and the tube clamp 15 is finally opened, the suction bottle 11 evacuates in the vacuum reducer 20 the space beneath the piston 25, causing the latter to move downward and to finally reach the inwardly projecting end of the shutoff fitting 24, abutting and sealing the latter. From this moment on, the intermediate suction space 27 between the bottom 22 and the piston 25 is separated from the shutoff fitting 24 and hence from the relatively high vacuum in the suction bottle 11. The intermediate suction space 27 is communicatively connected with the wound draining hose 12 by way of the inlet fitting 23 and the connecting tube 13 (FIG. 1). The pressure prevailing in the intermediate suction space 27 at the moment of such shutoff hence conforms to the effective suction pressure of the system.

The downward motion of the piston 25 in the way described above enlarges the volume of the gas enclosed above the piston, causing the pressure in such volume to drop. At the moment at which the piston 25 comes to rest on the shutoff fitting 24, the pressure on the underside of the piston 25, and hence the pressure in the intermediate suction space 27, substantially corresponds with the pressure in the space above the piston 25. Thus the suction pressure can be adjusted by said pressure in the upper space.

After the piston 25 has aligned itself flush with the shutoff fitting 24, two different vacuums act on its underside: the relatively high vacuum across the surface of the inside cross section of the shutoff fitting 24 and the lower vacuum in the intermediate suction space 27, which substantially corresponds with the vacuum in the upper space 28. So that the piston 25 can lift itself again from the shutoff fitting 24, the vacuum in the intermediate suction space 27, because of these conditions of the forces, has to become slightly lower than the value corresponding with the pressure in the upper space 28. Hence the intermediate suction space 27 is capable of sucking some wound secretion before the piston 25 lifts again from the shutoff fitting 24. As soon as the latter is the case, a connection is established again between the shutoff fitting 24 and the intermediate suction space 27, causing the vacuum in the intermediate suction space 27 to be reduced again until the piston 25 comes to rest again on the shutoff fitting 24, sealing the latter. For this system to function in a satisfactory manner, the volume formed by the intermediate suction space 27, the connecting tube 13 and the wound draining tube 12 has to be slightly compressible. This, as a rule, is the case because some gas is frequently enclosed in the wound secretion. For cases in which no gas might be transported with the secretion, it is advantageous if the piston 25, in particular the bottom of the piston is designed slightly pliable. Such an elastic piston 25 is shown also in FIG. 3. Its bottom is pliable to the extent that it acts like a diaphragm sealing the shutoff fitting 24, with the result that for functioning as a pressure controlling element, the entire piston need not move up and down; only the bottom of the piston has to lift slightly from the shutoff fitting 24 by deformation, and then come to rest again on the latter.

When a suction bottle 11 (FIG. 1) is almost completely full of secretion, the inside pressure finally rises, so that a state is finally reached in which, when the piston 25 lifts off the shutoff fitting 24, the amount of secretion aspirated from the intermediate suction space 27 through the shutoff fitting 24 no longer suffices to pull the piston 25 down again. From this moment on, a constant connection exists between the intermediate suction space 27 and the shutoff fitting 24. Now, when the suction bottle 11 is filling further, the vacuum on the bottom surface of the piston 25 falls off increasingly, causing the piston to increasingly move upward because of the vacuum in the upper space 28. The pressure prevailing at a given time can be read on a scale 29 on the outer side of the transparent hollow cylinder 21. FIG. 4 shows a vacuum reducer 20 with a piston position as it is assumed by the piston 25 when the suction pressure is already significantly above the suction pressure actually desired for steadily aspirating a large amount of secretion. Such a piston position is the sign alerting the nursing staff that the almost full suction bottle urgently needs to be replaced by a new bottle.

Figure 5:
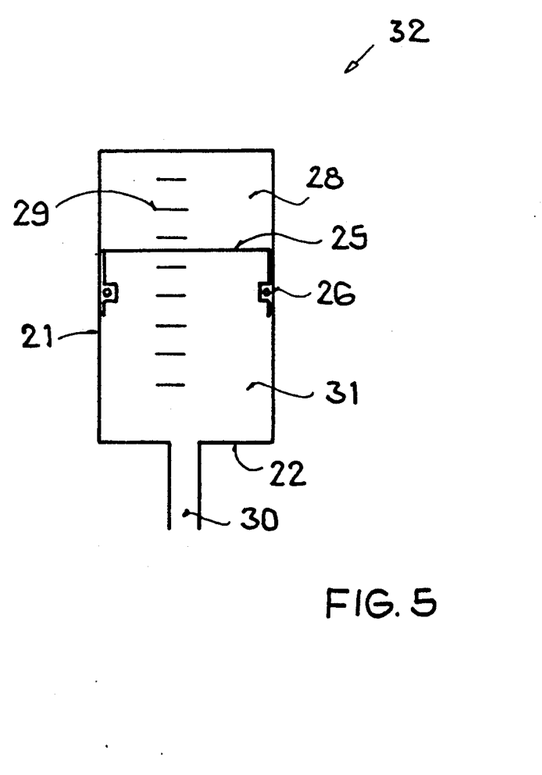
FIG. 5: is a schematic longitudinal section through a pressure indicator with a structure similar to the one of the vacuum reducer according to FIG. 3.

The above explanations show that the vacuum reducer 20 according to FIGS. 3 and 4 has not only the function of maintaining constancy, but also the function of a pressure indicator. In cases in which the function of maintaining constancy can be dispensed with, for example because a suction bottle 11 with pressure-adjusting liquid 16 or with a secretion-soluble gas filling is used, such function of maintaining constancy and hence the shutoff fitting 24 can be omitted. This, then, results in a construction as shown in FIG. 5, according to which a piston 25 operates in a closed hollow cylinder 21. A small amount of gas is again enclosed in the top space 28 above the piston 25. The lower space 31 beneath the piston 25 is connectable to parts of a suction system 10 (FIG. 1) via a connection fitting 30. When a vacuum is produced in the lower space 31, the piston 25 is caused to move upward until the pressure in the upper space 28 and the lower space 31 is the same. A scale 29 on the outer side of the hollow cylinder 32 shows the vacuum prevailing at the given time. This pressure indicator 32 according to FIG. 5 acts in the same way as the pressure indicator according to DE-C2-30 11 163, however, it has a much simpler structure because the force for resetting the piston 25 is made available by a gas volume and not by a spring.

Figure 6:
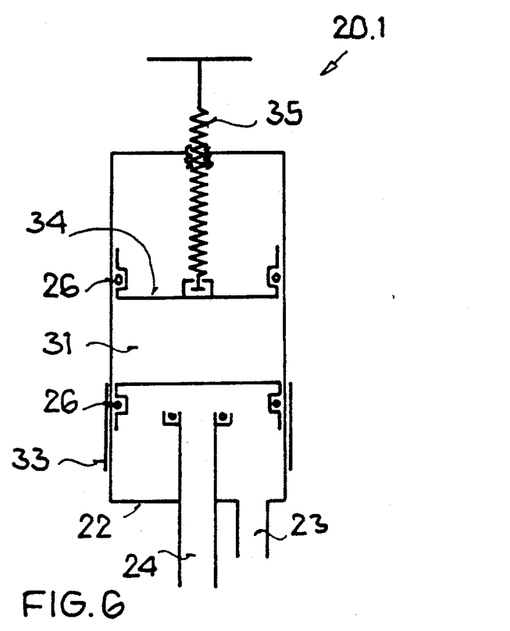
FIG. 6: is a schematic longitudinal section through a vacuum reducer with adjustable suction vacuum.

The adjustable vacuum reducer 20.1 according to FIG. 6 differs from the one according to FIGS. 3 and 4 in that, on the one hand, its lower range is covered by a non-transparent sleeve 33, so that the shutoff fitting 24 and the piston 25 sealing it are not visible. Only when the piston 25 vacates its shutting position due to vacuum decrease in the suction bottle 11 (FIG. 1) and moves upward does it become visible.

The second significant difference is that a pressure-adjusting piston 34 is present in the upper space 28. The position of this pressure-adjusting piston 34 is adjustable via a spindle 35. When the pressure-adjusting piston 34 is positioned relatively close to the shutting piston 25, a relatively low vacuum prevails in the space enclosed by the two pistons. When, on the other hand, the spacing between the two pistons is enlarged, the vacuum in the enclosed volume becomes increasingly higher. As the pressure in the intermediate suction space 27 beneath the pressure-adjusting piston 25 substantially corresponds with the pressure in the space above this piston 25, the suction vacuum can be adjusted by adjusting the pressure-adjusting piston 34. The pressure value can be read from a scale 29 on the hollow cylinder 21.

Figure 7:
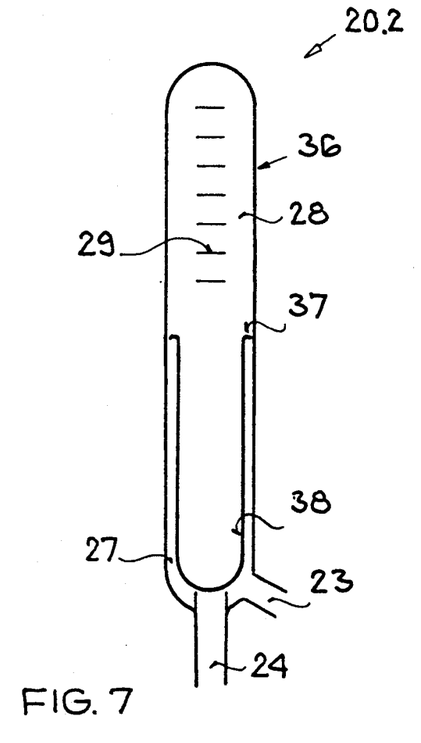
FIG. 7: is a longitudinal section through a vacuum reducer with a finger-shaped, flexible diaphragm as the valve component.
Figure 8:
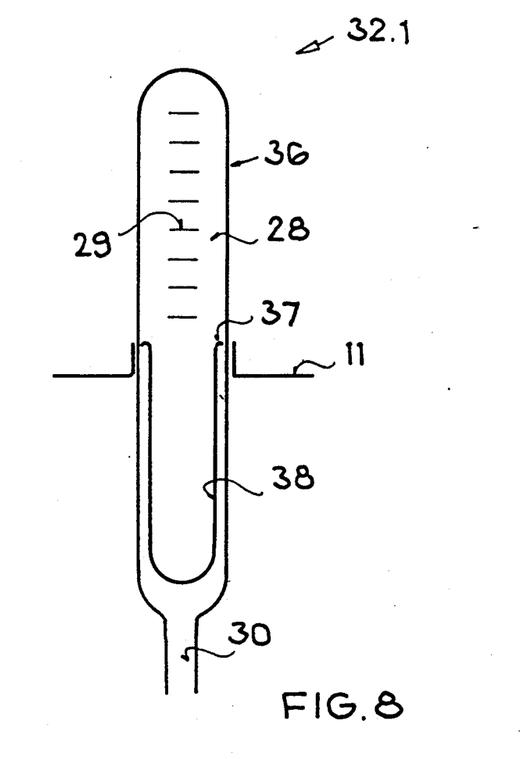
FIG. 8: is a cross section through a pressure indicator with a structure similar to the one of the vacuum reducer according to FIG. 7, in a position indicating maximum vacuum.
Figure 9:
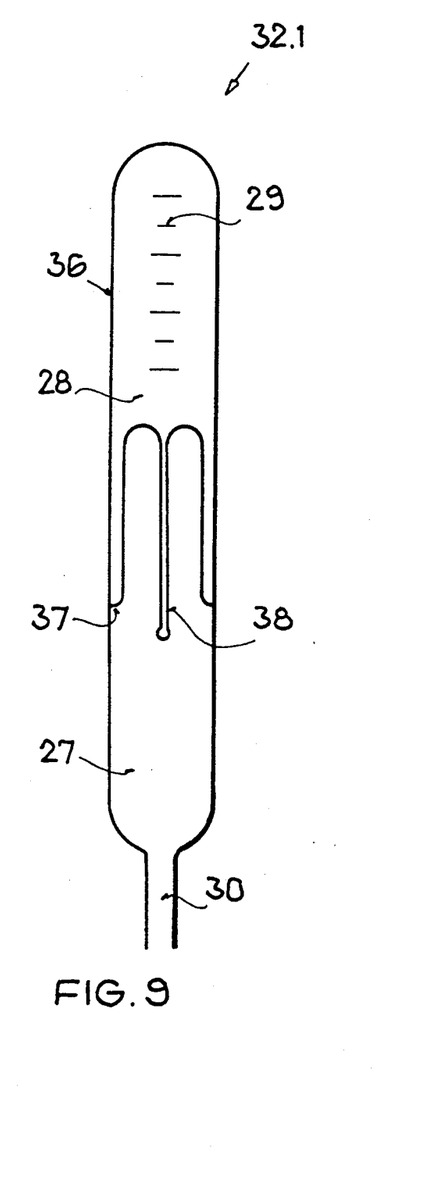
FIG. 9: is a longitudinal section through the pressure indicator according to FIG. 8, but in a position indicating the medium suction pressure.
Figure 10:
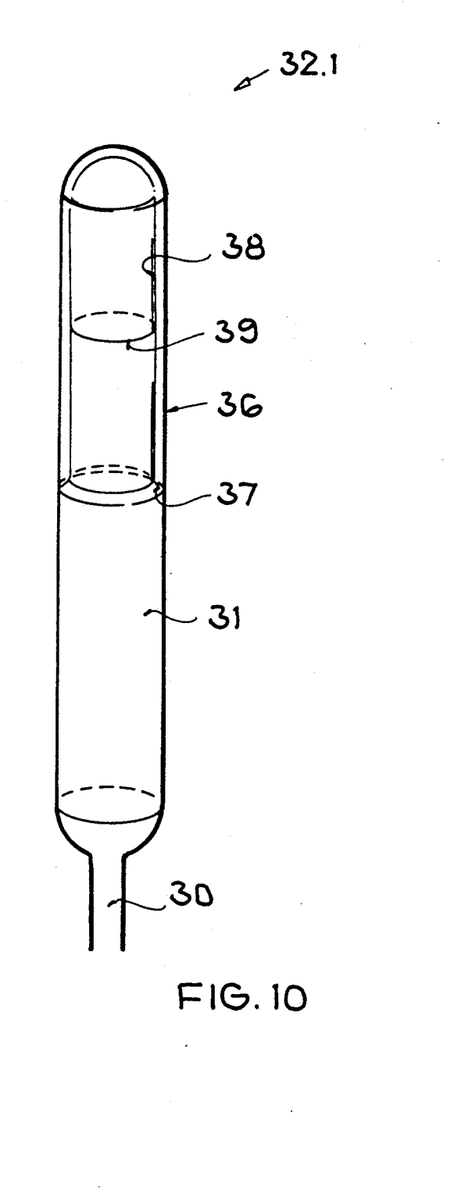
FIG. 10: is a perspective view of the vacuum reducer according to FIG. 8, but shown in a position indicating that the suction vacuum is no longer sufficient.

FIG. 7 shows another configuration of a combined vacuum reducer/pressure indicator. Embodiments with only the pressure indication function are shown in FIGS. 8 to 10. With all components according to FIGS. 7 to 10, provision is made for a transparent pressure indication tube 36, which is closed at its top. In the embodiment according to FIG. 7, the tube has a bottom penetrated and sealed by a shutoff fitting 24. An inlet fitting 23 is fitted laterally on the pressure indication tube 36 closely above the bottom. In the embodiments shown in FIGS. 8 to 10, the tube ends in a connection fitting 37. A finger-shaped diaphragm 38 made of flexible material is fastened gastight in about the center of the longitudinal extension of the pressure indication tube 36 along the zone of the entire inner circumference of the tube. Such fastening is accomplished in that the pressure indication tube 36 is divided in the center and glued together there, in a way such that the edge of the diaphragm is glued in, too. The diaphragm consists of a polyethylene foil, but it may consist of some other material as well, for example of a rubber material reinforced by an elastic fabric, or a flexible rubber material with, however, only limited elasticity. It is shaped in such a way that when in the resting position, it assumes the finger-like shape shown in FIG. 10. The outside diameter of the finger-shaped part of the diaphragm 38 is preferably slightly smaller than the inside diameter of the pressure indication tube 36.

In the embodiment according to FIG. 7, the lower end of the diaphragm 38 seals the shutoff fitting 24. In this position, the function of the diaphragm corresponds with the function of the piston 25 in its position shown in FIG. 3. Hence the predetermined vacuum section is adjusted on the inlet fitting 23 in the same way as with the vacuum reducer 20 according to FIGS. 3 and 4. Reference is made to the description of these figures.

If the vacuum on the shutoff fitting 24 falls off to a value too low for the diaphragm 38 to seal such fitting, the combined vacuum reducer 20.2 with diaphragm changes to the pressure indication function, which is described in the following with reference to FIGS. 8 to 10 for a pressure indicator 32.1 which, as stated above, comprises only a connection fitting 30 instead of an inlet fitting 23 and a shutoff fitting 24.

As long as a sufficiently high vacuum is applied to the connection fitting 30 (or to the shutoff fitting 24), the diaphragm is in the downwardly extended position as shown in FIG. 8 (or 7). A small amount of gas is trapped in the space 28 above the diaphragm 38, which space is sealed gastight. When the diaphragm is in the downwardly extended position, such gas has a predetermined vacuum. When the vacuum on the connection fitting 30 becomes lower than the vacuum in the upper space 28, the diaphragm 38 is forced upward, reducing the volume of the upper space 28 and causing the gas pressure in such space to rise again until it is in equilibrium again with the pressure on the connection fitting 30. The lower the vacuum on the connection fitting 30 the more the finger-like diaphragm is folded together first lengthwise, and then rolled through its fastening collar 37 in order to subsequently turning itself out again into the space above the collar, as this is shown for a position in FIG. 9. The position of the diaphragm conforms to the indication of the volume of a defined quantity of gas. Such volume is a function of the pressure beneath the diaphragm 38. At atmospheric pressure below the diaphragm, the latter assumes again its original finger-like shape as shown in FIG. 10.

The position of the diaphragm 38 is easily visible even from a distance if the pressure indicator 32.1 or combined vacuum reducer 20.2 are sufficiently large. Such good visibility of the indication is enhanced further in a preferred configuration in that color markings are attached to both sides of the diaphragm. In the following, the side of the diaphragm that is visible at atmospheric pressure - thus with the position according to FIG. 10 - is referred to as the outer side. The inner side, on the other hand, is the side visible after the diaphragm has rolled itself all the way down through its fastening collar 37. This inner side is colored green, whereas the outer side is colored yellow across approximately half of its length up to the marking line 39, from the fastening collar 37 to such marking line 39, and colored red on top. As the vacuum in the draining system falls off, first the length of the green outer side visible to the eye decreases due to the motion of the diaphragm 38. Subsequently, a yellow column becomes visible, which is finally joined upwardly by a red column. At the latest, the suction bottle 11 in suction system 10 (FIG. 1) should be replaced when the yellow column appears. For a more accurate reading of the pressure, provision may be made for a scale on the pressure indication tube 36, such a scale being calibrated in pressure units.

The vacuum reducers and pressure indicators according to FIGS. 7 to 10 may be used as separate system components, but they also may be rigidly connected with a suction bottle 11. An example of the latter is shown in FIG. 8: the suction bottle 11, of which only a short zone of its top edge is shown, has a mounting fitting 40 into which a tubular pressure indicator 32.1 is glued in such a way that the point of glueing is disposed approximately in the center of the lengthwise direction of the pressure indicating tube 36. This saves structural height, as only half of the pressure-indicating tube 36 projects outward beyond the suction bottle 11. In such a configuration, the lower part of the pressure-indicating tube 36 can be dispensed with entirely, as it is no longer required for protecting the diaphragm 38. In this case, the diaphragm together with the outward projecting pressure indication tube can be directly glued to the mounting fitting 40. With such mounting, too, the green inner wall of the diaphragm 38 turned inside out into the suction bottle is still easily visible because suction bottles are made of transparent plastic material.

Figure 11:
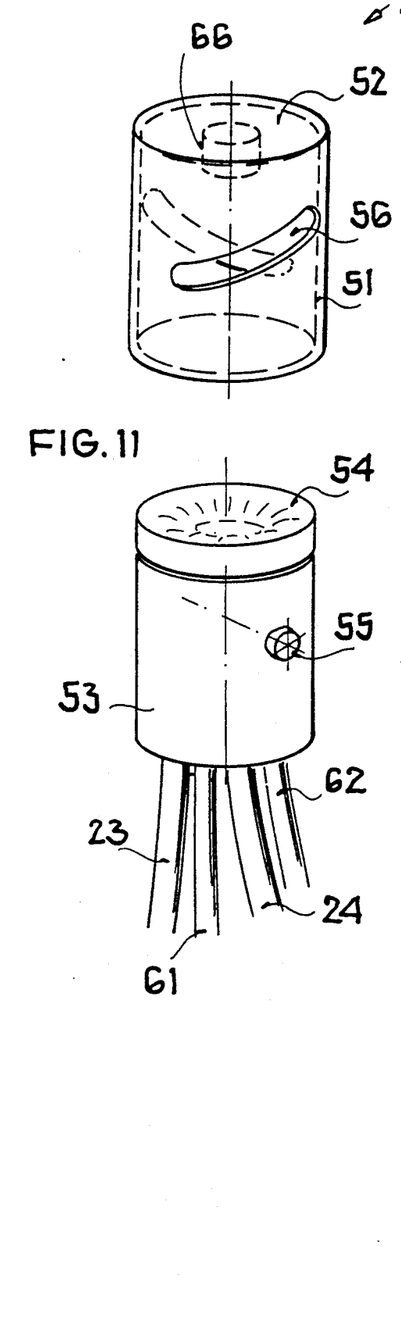
FIG. 11: is an exploded perspective view of a connection system.
Figure 12:
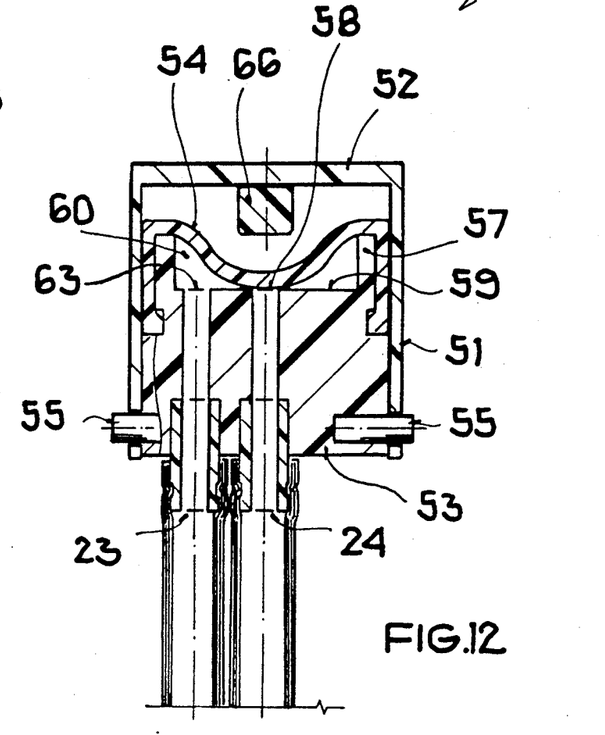
FIG. 12: is a cross section through the assembled device according to FIG. 1.
Figure 13:
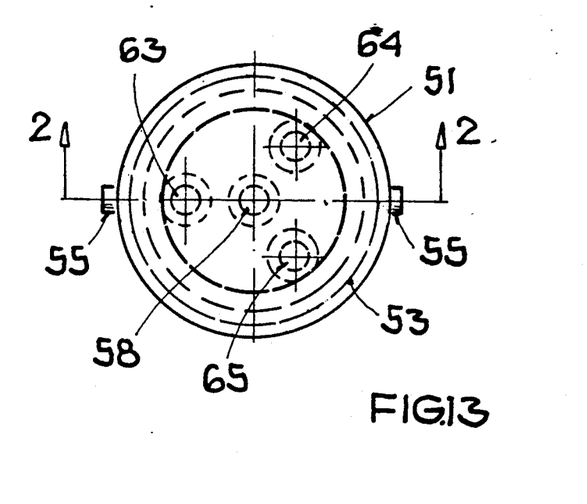
FIG. 13: is a top view of the diaphragm holder contained in FIGS. 11 and 12.

The connection system 50 according to FIGS. 11 and 12 has a hollow cylinder 51 which, on the one side, is sealed by a closing wall 52. A diaphragm holder 53 with a diaphragm 54 operates in the hollow cylinder 51. Such a diaphragm 54 is fastened on the diaphragm holder and directed against the closing wall 52, sealing the latter against the hollow cylinder 51. The diaphragm holder 53 is displaced via a screw connection formed by two pins 55 on the diaphragm holder 53, such two pins gripping through two screw-like recesses 56 in the hollow cylinder 51.

The diaphragm holder 53 is designed in such a way that it has a rotating bead 57 at the face side on which the diaphragm is fastened. A center opening 58 communicating with an outward leading shutoff fitting 24 feeds into the center of such face side. Due to the presence of such a bead 57, the latter and the face side 59 of the diaphragm 53 and the inner side of the diaphragm 54 enclose a hollow space 60, which is accessible via the center opening 58 as long as the diaphragm 54 has not been deformed against the face side 59 to an extent such that it closes the center opening 58.

In the configuration shown, the openings of three additional fittings feed into the hollow space 60: the opening of an inlet fitting 23, of a vacuum indicator fitting 61, and of an overflow fitting 62. The associated openings are an inlet opening 63, a measuring opening 64, and an overflow opening 65, respectively.

Now, it is assumed that a vacuum indicator is connected with the vacuum indicator fitting 61, and an overflow receptacle with the overflow fitting 62. Both devices should have a small volume, so that a vacuum can be produced therein quickly. It is assumed, furthermore, that the inlet fitting 23 is communicatively connected with a perforated wound draining tube, and that the inlet fitting 23 is connected to a suction bottle. Such connection is made with the connection system in a position in which the diaphragm holder 53 is disposed close to the closing wall 52 of the hollow cylinder 51, so that an elastic sealing part 66, which is mounted on the inside of the closing wall 52, forces the diaphragm 54 against the center opening 58. Now, when the hollow cylinder 51 is screwed into position against the diaphragm holder 53, its closing wall 52 moves away from the diaphragm 54, causing a vacuum to build up in the space in between. When such vacuum finally applies a force to the diaphragm that is greater than the counterforce applied by the vacuum on the shutoff fitting 24 across the area of the center opening 58, the diaphragm 54 lifts from the center opening 58, whereupon air and secretion are aspirated from the hollow space 60 via the shutoff fitting 24 until the force exerted on the diaphragm 54 from the side of the hollow space exceeds the counterforce acting upon the outer side of the diaphragm 54, and the latter again covers the center opening 58.

The pressure in the hollow space 60 at which the diaphragm 54 lifts from the center opening 58 depends not only on the pressure on the outer side of the diaphragm 54 and the pressure on the center opening 58, but also upon the elastic force acting upon the diaphragm 54, the latter being pulled over the bead 57. Hence the degree of vacuum in the hollow space 60 can be preselected by predetermining such elastic force, and finely adjusted by displacing the hollow cylinder 51 and the diaphragm holder 53 against each other. For setting the elastic force it is possible to modify the material of the diaphragm 54 or its shape, or the height of the bead 57 and its inside diameter can be varied.

If the connection between a wound draining tube and a suction bottle has to be completely interrupted, e.g. for replacing the suction bottle, the diaphragm holder 53 and the hollow cylinder 51 are again turned against each other until the sealing part 66 forces the diaphragm 54 against the center opening 58, as in the starting position. In such a condition, secretion can still drain via the inlet opening 63 and the overflow opening 65 into the overflow fitting 62, and from there into an overflow receptacle.

As explained above, the adjustability between the hollow cylinder 51 and the diaphragm holder 53 serves for finely adjusting a desired vacuum. If such fine adjustment can be omitted, the displaceability between the hollow cylinder 51 and diaphragm holder 53 can be dispensed with as well, or the hollow cylinder 51 can be entirely omitted. In that case, the vacuum obtainable in the hollow space 60 and hence the vacuum suction in the round draining tube is determined only by the elastic force exerted by the diaphragm 54. Such a design has no bearing on the arrangement of fittings.

The adjustability between the diaphragm holder 53 and the hollow cylinder 51 can be obtained through any number of displacement designs. For example, instead of having pins gripping through recesses, provision may be made for shorter pins which only engage screw-like grooves in the inner circumferential wall of the hollow cylinder. Also, any other screw connection may be selected for joining the hollow cylinder and the diaphragm holder. Furthermore, lock and catch connections may be used, with which such parts are fixed upon displacement in a new position by locking forces.

What is claimed is:

1. A device for aspirating wound liquids, comprising a suction bottle with a connection system for the suction bottle embodied as a suction controlling device including:

a diaphragm;

a circular cylindrical diaphragm holder, of which an upper face is covered by the diaphragm with clearance between said upper face and said diaphragm for a hollow space, wherein a center opening and at least one additional opening feed into the upper face in a way such that each of said at least one additional opening is not covered by the diaphragm when the diaphragm closes the center opening; and a circular cylindrical hollow cylinder closed on top by a closing wall and having the diaphragm holder with the diaphragm guided in its interior back and forth in the lengthwise direction, such diaphragm sealing against the inner wall of the cylinder.

2. The device as claimed in claim 1, wherein a small quantity of a liquid is present in the bottle, the vapor pressure of said liquid conforming to a desired vacuum level, said level being constant substantially throughout the entire filling process of the bottle.

3. The device as claimed in claim 2, wherein the liquid is a mixture of pentane and hexane.

4. The device as claimed in claim 2, wherein the bottle contains a predetermined amount of gas with a vapor pressure less than air thus creating a desired vacuum level, said gas being capable of dissolving in an aspirated secretion.

5. The device as claimed in claim 4, wherein said gas is $CO_2$.

6. The device as claimed in claim 2, wherein said suction bottle has a bottom piercable by a cannula.

7. The device as claimed in claim 2, wherein the bottle contains a predetermined amount of gas with a vapor pressure less than air, thus creating desired vacuum level, said gas being capable of entering into a chemical bond with an aspirated secretion.

8. The device as claimed in claim 7, wherein said gas is $CO_2$.

9. The device as claimed in claim 4, wherein said gas is capable of dissolving in an aspirated secretion is capable of entering into a chemical bond with the latter.

10. The device as claimed in claim 9, wherein said gas is $CO_2$.

11. The device as claimed in claim 1, wherein the diaphragm holder is joined with the hollow cylinder via a screw connection.

12. The device as claimed in claim 11, wherein the screw connection is formed in that at least one pin is present on the diaphragm holder, said pin engaging a screw-like recess in the wall of the hollow cylinder.

13. The device as claimed in claim 1, wherein an elastic sealing part is mounted in the center of the inner side of the closing wall of the hollow cylinder.

14. A device for aspirating wounds liquids, comprising a suction bottle with a connection system for the suction bottle embodied as a suction controlling system including:
- a diaphragm;
- a circular cylindrical diaphragm holder, of which an upper face is covered by the diaphragm with clearance between said upper face and said diaphragm for a hollow space, wherein a center opening and at least two additional openings feed into the upper face in a way such that each of said at least two additional openings is not covered by the diaphragm when the diaphragm closes the center opening; and
- a circular cylindrical hollow cylinder closed on top by a closing wall and having the diaphragm holder with the diaphragm arranged in its interior in a way such that the diaphragm seals against the inner wall of the cylinder.

* * * * *